United States Patent [19]

Saxton et al.

[11] Patent Number: 5,412,122

[45] Date of Patent: May 2, 1995

[54] EPOXIDATION PROCESS

[75] Inventors: Robert J. Saxton, West Chester; John G. Zajacek, Devon, both of Pa.; Guy L. Crocco, Wilmington, Del.

[73] Assignee: Arco Chemical Technology, L.P., Greenville, Del.

[21] Appl. No.: 172,404

[22] Filed: Dec. 23, 1993

[51] Int. Cl.⁶ .................. C07D 301/12; C07D 303/04
[52] U.S. Cl. .................................... 549/531; 568/672
[58] Field of Search ......................... 549/531

[56] References Cited

U.S. PATENT DOCUMENTS

| | | | |
|---|---|---|---|
| 4,410,501 | 10/1983 | Taramasso et al. | 423/326 |
| 4,576,805 | 3/1986 | Chang et al. | 423/277 |
| 4,666,692 | 5/1987 | Taramasso et al. | 423/326 |
| 4,828,812 | 5/1989 | McCullen et al. | 423/326 |
| 4,833,260 | 5/1989 | Neri et al. | 549/531 |
| 5,098,687 | 3/1992 | Skeels et al. | 423/328 |
| 5,221,795 | 6/1993 | Clerici et al. | 549/531 |
| 5,233,097 | 8/1993 | Nemeth et al. | 568/803 |
| 5,246,690 | 9/1993 | Bellussi et al. | 423/705 |
| 5,252,758 | 10/1993 | Clerici et al. | 549/531 |
| 5,310,534 | 5/1994 | Fajula et al. | 423/715 |

FOREIGN PATENT DOCUMENTS

| | | | |
|---|---|---|---|
| 1128540 | 7/1982 | Canada | 549/531 |
| 190609 | 8/1986 | European Pat. Off. | 549/531 |
| 230949 | 8/1987 | European Pat. Off. | 549/531 |
| 2694549 | 8/1992 | France . | |
| 2037596 | 7/1991 | Spain . | |
| WO8504856 | 11/1985 | WIPO . | |
| WO94402245 | 2/1994 | WIPO . | |

OTHER PUBLICATIONS

Journal of Catalysis, 145 A. Corma et al. pp. 151-158 (1994).
Catalysis Letters 1, B. Kraushaar et al. pp. 85-92 (1988).
Heterogeneous Catalysis, R. Schlög, pp. 381-383 (1993).
Chemical Communications 8, M. A. Cambber et al., pp. 589-590 (1992).
Journal of Catalysis 130, A. Thangaraj et al. pp. 1-8 (1991).
Zeolites, vol. 13 "Synthesis of titanoaluminosilicates etc.", M. A. Cambbor et al., pp. 82-87 (1993).
Symposium on Chemically Modified Molecular Sieves, Div. Pat. Chem. 206th Annual Meeting "Syntheis and Physiochemical etc.", C. B. Dartt et al., pp. 491-493 (1993).
Microporous Materials, vol. 1, "Single Step Doalumination etc.", E. Lami et al., pp. 237-244 (1993).

Primary Examiner—Joseph E. Evans
Attorney, Agent, or Firm—Stephen D. Harper

[57] ABSTRACT

Olefins are epoxidized by hydrogen peroxide in the presence of a modified titanium-containing molecular sieve having a framework structure isomorphous with zeolite beta and comprised of Si, Ti, and Al. The molecular sieve is modified by substituting the aluminum-associated cationic sites with ammonium, alkali metal, or alkaline earth cations instead of protons.

15 Claims, No Drawings

EPOXIDATION PROCESS

FIELD OF THE INVENTION

This invention relates to methods of selectively oxidizing olefins so as to obtain products containing epoxide functional groups. In particular, the invention pertains to processes whereby a hydrogen peroxide source is reacted with an ethylenically unsaturated substrate in the presence of a relatively large pore crystalline titanium-containing molecular sieve catalyst to yield an epoxide. The catalyst is characterized by a framework structure isomorphous to zeolite beta comprised of Si, Ti, and Al atoms. At least a portion of the aluminum-associated cationic sites are substituted with ammonium, alkali metal, or alkaline earth cations instead of protons.

BACKGROUND OF THE INVENTION

Many different methods for the preparation of epoxides have been developed. One such method involves the epoxidation of an olefin in a liquid phase reaction using an organic hydroperoxide as the oxidizing agent and certain solubilized transition metal compounds as catalyst. Although this approach is practiced commercially and generally provides high selectivity to epoxide, it has at least two characteristics which tend to limit process flexibility and increase production costs. The use of an organic hydroperoxide results in the generation of a co-product alcohol derived from the reacted hydroperoxide during epoxidation; approximately 1 equivalent of the co-product is obtained for each equivalent of epoxide. If no market exists for the alcohol, the co-product must either be further reacted (incurring additional processing costs) so as to convert it back to the hydroperoxide oxidant or to another compound for which a commercial demand exists. Recovery of the soluble metallic catalyst used in such a process for reuse in subsequent runs is also problematic. It would therefore be highly desirable to develop an insoluble (heterogeneous) epoxidation catalyst which has high activity and selectivity when utilized with an oxidant such as hydrogen peroxide which does not form an organic co-product. Such a catalyst would ideally be readily recoverable in active form from an epoxidation reaction mixture by filtration or similar separation techniques or be capable of being utilized in the form of a fixed bed or the like.

Workers at the Universidad Politecnica de Valencia have recently reported the synthesis of a titanium silicoaluminate isomorphous to zeolite beta (see Camblor et al., *J. Chem. Soc., Chem. Commun.* pp. 589–590 (1992), Camblor et al., *Zeolites* 13, pp. 82–87 (1993) and ES 2037596 (published 6/16/93)). Such materials were found to catalyze the oxidation of alkanes to alcohols, ketones, and the like using hydrogen peroxide as the oxidant. This type of titanium silicoaluminate in unmodified (fully protonated) form is a poor catalyst for the production of epoxides from olefins, however.

Titanium silicalite, a zeolite of the ZSM family, is known to be an efficient epoxidation catalyst with hydrogen peroxide. In titanium silicalite, Ti atoms are located in vicariant positions in place of Si atoms in the crystalline framework. As noted in Romano et al., "Selective Oxidation with Ti-silicalite", *La Chemica & L'Industria* 72, 610–616, however, no Al atoms are present in titanium silicalite. The presence of Al atoms creates strongly acidic sites. As acids are known to catalyze epoxide ring-opening reactions, it was heretofore believed that a zeolite containing aluminum could not provide high yields of epoxide when employed as an olefin epoxidation catalyst since considerable amounts of by-products resulting from epoxide decomposition would result.

SUMMARY OF THE INVENTION

We have now made the unexpected discovery that a crystalline titanium-containing molecular sieve (zeolite) characterized by a framework structure isomorphous to zeolite beta and comprised of Si, Ti, and Al atoms can selectively catalyze the epoxidation of olefins using hydrogen peroxide or a hydrogen peroxide precursor. Selectivity to epoxide is significantly enhanced when at least 25% of the cations present at the aluminum-associated cationic sites are ammonium, alkali metal, or alkaline earth metal cations rather than hydrogen cations (i.e., protons). The substitution of cations such as $K^+$ and $Na^+$ for the protons present in unmodified titanium silicoaluminates unexpectedly improves selectivity to epoxide, with the formation of undesired by-products such as glycol or glycol ethers being suppressed.

DETAILED DESCRIPTION OF THE INVENTION

In the process of this invention, an olefin is contacted with hydrogen peroxide or a substance capable of producing hydrogen peroxide under the reaction conditions in the presence of a catalytically effective amount of an ammonium, alkali metal, or alkaline earth-modified titanium-containing molecular sieve. The titanium-containing molecular sieve suitable for use is characterized by a framework structure isomorphous to zeolite beta. Si, Ti, and Al atoms are present in the framework structure (typically, in the form of oxides). The presence of aluminum atoms creates cationic sites associated with aluminum. The cations present at said cationic sites are selected from hydrogen cations, ammonium cations, alkaline earth metal cations, and alkali metal cations, but at least 25% (more preferably, at least 50%; most preferably, at least 75%) of said cations are ammonium, alkali metal or alkaline earth cations. Correspondingly, the proportion of such cations which are hydrogen cations should be no more than 75% (more preferably, no more than 50%; most preferably, no more than 25%).

Zeolite beta is characterized by 12-member ring pore openings and a three dimensional interconnecting channel system; its framework structure is more completely described in U.S. Pat. No. 3,308,069, Szostak, *Handbook of Molecular Sieves*, pp. 92–96, Higgin et al., *Zeolites*, 8, 446 (1986), and Treacy et al., *Nature*, 332, 249 (1988). The catalyst utilized in the present invention thus has a fundamentally different structure than other titanium-containing molecular sieves reported in the prior art (e.g., the TS-1 catalyst described in U.S. Pat. No. 4,410,501, which has an MFI structure; the TS-2 catalyst described by Reddy et al. in *Appl. Cat.* 58, L1 (1990) which has a ZSM-11 structure).

Alkali metal (Group IA) cations are preferred for use in replacing the hydrogen cations, most preferably sodium ($Na^+$), potassium ($K^+$), or combinations thereof. Suitable alkaline earth metal (Group IIA) cations include $Ca^{+2}$ and $Mg^{+2}$. The ammonium cation may be $NH_4^+$ or some organic analog thereof such as quaternary ammonium. In preferred embodiments, the titanium-containing molecular sieve has relatively large pores (equal to or greater than about 6 angstroms on average) and has a zeolite-type structure comprised of Si and smaller amounts of Ti and Al in a crystalline ordered framework. A crystallinity of greater than 80% is usually desirable. Preferably, the molar ratio of Ti:Si is from 0.1:99.9 to 20:80, with ratios in the range of 0.5:99.5 to 10:90 being especially preferred. The molar ratio of (Si+Ti): Al is desirably at least 25:1 (more preferably, at least 100:1). In one advantageous embodiment, the Si/Al molar ratio is greater than 25 but less than 1000. Generally speaking, as the aluminum content is increased at a constant titanium level, the epoxidation rate tends to decrease. Moreover, the epoxidation becomes less selective. Without wishing to be bound by theory, it is believed that these trends are attributable to the competition of Al sites with Ti sites for the hydrogen peroxide. The titanium-containing molecular sieve advantageously may have a titanium content of from 1 to 10 weight percent and an aluminum content of from 0.02 to 2 weight percent.

The general formula for the titanium-containing molecular sieve (exclusive of any ammonium, alkali metal or alkaline earth metal cations introduced by modification) is preferably as follows:

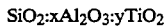

$SiO_2:xAl_2O_3:yTiO_2$ wherein x is 0.0005 to 0.2 and y is from 0.01 to 0.2.

The porous titanium-containing molecular sieves suitable for use as epoxidation catalysts in the present invention may be obtained by any method known in the art. If a titanium-containing molecular sieve containing significant amounts of aluminum is desired, the procedures described in the aforementioned publications by Camblor and co-workers (the teachings of which are incorporated herein by reference in their entirety) may be employed. For instance, a mixture comprised of water, a titanium tetraalkoxide such as titanium tetraethoxide (or another source of titanium oxide such as a hydrolyzable titanium halide), a organophosphonium or organoammonium salt template such as tetraethyl ammonium hydroxide or tetraethyl phosphonium hydroxide, an aluminum salt such as aluminum nitrate nonahydrate, and silica gel (amorphous silica) or some other source of $SiO_2$ such as a tetraalkylorthosilicate or inorganic silicate (e.g., alkali metal silicate), the mixture preferably being essentially free of alkali metals and alkaline earth metals, may be subjected to hydrothermal treatment at a temperature in the range of 75° C. to 200° C. for a time effective to obtain precipitated crystals and a mother liquor (supernatant). The precipitated crystals are separated from the mother liquor, washed (if desired), and then calcined (either in an inert atmosphere or in an oxygen-containing atmosphere) at an elevated temperature (typically, 350° to 800° C.). The calcined crystals of titanium silicoaluminate thus obtained are essentially free of the quaternary salt template and have aluminum-associated cationic sites wherein the cations present at said cationic sites are hydrogen cations.

To modify the calcined crystals prepared as described above to obtain an active catalyst which will selectively transform olefins to epoxides using hydrogen peroxide or an equivalent thereof, the calcined crystals may be contacted with an ammonium, alkali metal and/or alkaline earth metal compound under conditions effective to replace at least a portion (preferably, at least 25%; more preferably, at least 50%; most preferably, at least 75%) of the hydrogen cations present at the aluminum-associated cationic sites with ammonium, alkali metal, and/or alkaline earth metal cations. A preferred method for accomplishing this modification is to dissolve the ammonium, alkali metal or alkaline earth metal compound in water or other suitable liquid medium; the resulting solution is then brought into intimate contact with the calcined crystals. This procedure should be performed at a temperature sufficiently high so as to accomplish the partial or complete exchange or replacement of the ammonium, alkali metal or alkaline earth metal for the hydrogen cations within a practicably short period of time (e.g., within 24 hours). For this purpose, temperatures of from about 25° C. to 150° C. will generally suffice. The concentration of ammonium, alkali metal or alkaline earth metal compound in the liquid medium may be varied as desired and will typically be from about 0.001 to 5 molar. Optimum concentrations may be readily ascertained by routine experimentation. Following the desired cation exchange, the excess liquid medium may be separated from the modified titanium-containing molecular sieve by filtration, decantation, centrifugation, or other such technique, and the modified titanium-containing molecular sieve washed (if desired) with water or other liquid substance, and then dried and/or calcined prior to use in the epoxidation process of this invention. If an ammonium compound has been utilized, calcination is preferably avoided so as to minimize any re-protonation of the catalyst.

The particular ammonium, alkali metal or alkaline earth metal compound selected for use is not critical but preferably is water-soluble and is desirably selected from ammonium, alkali metal or alkaline earth metal hydroxides and oxides (e.g., sodium hydroxide, potassium hydroxide, barium hydroxide, calcium hydroxide), ammonium, alkali metal or alkaline earth metal carbonates (e.g., sodium carbonate, potassium carbonate), ammonium, alkali metal or alkaline earth metal bicarbonates (e.g., sodium bicarbonate, potassium bicarbonate), ammonium, alkali metal or alkaline earth metal nitrates (e.g., sodium nitrate, potassium nitrate), ammonium, alkali metal or alkaline earth metal halides (e.g., potassium chloride, sodium bromide, sodium chloride), ammonium, alkali metal or alkaline earth metal sulfates (e.g., sodium sulfate, potassium sulfate), ammonium, alkali metal or alkaline earth metal salts of carboxylic acids (e.g., sodium acetate), and the like and mixtures thereof. The counter anion in the ammonium, alkali metal or alkaline compound should be chosen such that it does not interfere with the desired epoxidation activity of the modified titanium-containing molecular sieve nor detrimentally alter its crystalline structure. For example, it has been found that under certain conditions the use of alkali metal pyrophosphates may deactivate or poison the molecular sieve catalyst.

Another suitable method for the preparation of the modified titanium-containing molecular sieves useful in the process of this invention involves a procedure wherein zeolite beta is partially dealuminated and the framework vacancies created by dealumination filled by titanium atoms. Post-synthesis dealumination methods are well-known and include, for example, reaction with mineral acids (e.g., HCl, $H_2SO_4$, $HNO_3$), carboxylic acids or chelating agents and hydrothermal or steaming treatments (possibly combined with acid leaching). See, for example, the extensive listing of publications describing zeolite dealumination methods catalogued in U.S. Pat. No. 4,576,805 (col. 8, line 62 through col. 9, line 27) and Scherzer, "The Production and Characterization of Aluminum-Deficient Zeolites", *ACS Symp. Ser.*, 248, 157–200 (1984). A particularly preferred method employs treatment of zeolite beta with nitric acid (preferably, 2 to 13M) at a temperature of from 25° C. to 150° C. for a period of time of from 5 minutes to 24 hours. Other mineral and arboxylic acids could alternatively be used, as described, for example, in British Pat. No. 1,061,847, European Pat. Publication No. 488,867, Krauschaar et al., *Catalysis Letters* 1, 81–84 (1988), Chinese Pat. No. 1,059,701 (*Chem. Abst.* 117:114655g), European Pat. Publication No. 95,304, and Chinese Pat. No. 1,048,835 (*Chem. Abst.* 115:52861u). The beta zeolite is desirably suspended in or otherwise contacted with a relatively large volume of the nitric acid (preferably, from 10 to 1000 parts by weight nitric acid per 1 part by weight of the zeolite beta). Suitable dealumination methods of this type are described in more detail in Lami et al., *Microporous Materials* 1, 237–245 (1993), and European Pat. Publication No. 488,867. The dealuminated material may thereafter be contacted with a titanium source. For example, the dealuminated zeolite beta may be exposed to a volatile titanium source such as $TiCl_4$ vapor in nitrogen for 1 to 24 hours at an elevated temperature (preferably, 250° C. to 750° C.). A liquid phase source of titanium such as $(NH_4)_2 TiF_6$ (aq.) or $TiF_4$(aq.) may alternately be utilized to insert Ti atoms into the framework vacancies of the dealuminated zeolite beta. Methods of post-synthesis titanium incorporation into zeolite materials are described, for example, in U.S. Pat. No. 4,576,805, U.S. Pat. No. 4,828,812, and Kraushaar, et al., *Catal. Lett.* 1, 81084 (1988). It may be desirable to then treat the titanium-containing molecular sieve with an ammonium salt such as ammonium nitrate, acid solution (such as aqueous nitric acid) or the like to convert the titanium source to acid form (i.e., hydrogen or hydronium form) or to remove extra-framework aluminum. Water-washing, drying, and/or calcination may also be advantageous. Partial or full substitution of ammonium, alkali metal, or alkaline earth metal cations for the hydrogen cations present at the aluminum-associated cationic sites is performed using any of the methods described previously herein to realize a highly selective epoxidation catalyst useful in the process of this invention. Cation exchange may also take place at sites within the molecular sieve other than the aluminum-associated cationic sites.

The amount of catalyst employed is not critical, but should be sufficient so as to substantially accomplish the desired epoxidation reaction in a practicably short period of time. The optimum quantity of catalyst will depend upon a number of factors including reaction temperature, olefin reactivity and concentration, hydrogen peroxide concentration, type and concentration of organic solvent as well as catalyst activity. Typically, however, the amount of catalyst will be from 0.001 to 10 grams per mole of olefin. The concentration of titanium in the total epoxidation reaction mixture will generally be from about 10 to 10,000 ppm.

The catalyst may be utilized in powder, pellet, microspheric, monolithic, extruded, or any other suitable physical form. The use of a binder (co-gel) or support in combination with the titanium-containing molecular sieve may be advantageous. Supported or bound catalysts may be prepared by the methods known in the art to be effective for zeolite catalysts in general.

Illustrative binders and supports (which preferably are non-acidic in character) include silica, alumina, silica-alumina, silica-titania, silica-thoria, silica-magnesia, silica-zironia, silica-beryllia, and ternary compositions of silica with other refractory oxides. Also useful are clays such as montmorillonites, koalins, bentonites, halloysites, dickites, nacrites, and anaxites. The proportion of titanium-containing molecular sieve to binder or support may range from 99:1 to 1:99, but preferably is from 5:95 to 80:20. The catalyst may also be impregnated or admixed with a noble metal such as Pt, Pd, and the like; such catalysts may be useful for redox-type reactions.

The olefin substrate epoxidized in the process of this invention may be any organic compound having at least one ethylenically unsaturated functional group (i.e., a carbon-carbon double bond) and may be a cyclic, branched or straight chain olefin. The olefin may contain aryl groups (e.g., phenyl, naphthyl). Preferably, the olefin is aliphatic in character and contains from 2 to 30 carbon atoms (i.e., a $C_2-C_{30}$ olefin). The use of light (low-boiling) $C_2$ to $C_{10}$ aliphatic mono-olefins is especially advantageous. More than one carbon-carbon double bond may be present in the olefin; dienes, trienes, and other polyunsaturated substrates thus may be used. The double bond may be in a terminal or internal position in the olefin or may alternatively form part of a cyclic structure (as in cyclohexene, for example). Other examples of suitable substrates include unsaturated fatty acids or fatty acid derivatives such as esters or glycerides and oligomeric or polymeric unsaturated compounds such as polybutadiene. Benzylic and styrenic olefins may also be epoxidized, although the epoxides of certain styrenic olefins such as styrene may further react or isomerize under the conditions utilized in the present invention to form aldehydes and the like.

The olefin may contain substituents other than hydrocarbon substituents such as halide, carboxylic acid, ether, hydroxy, thiol, nitro, cyano, ketone, acyl, ester, anhydride, amino, and the like.

Exemplary olefins suitable for use in the process of this invention include ethylene, propylene, the butenes (e.g., 1,2-butene, 2,3-butene, isobutylene), butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinyl cyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters) and the like.

Mixtures of olefins may be epoxidized and the resulting mixtures of epoxides either employed in mixed form or separated into the different component epoxides.

The process of this invention is especially useful for the epoxidation of $C_2$–$C_{30}$ olefins having the general structure

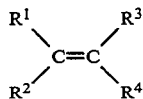

wherein $R^1$, $R^2$, $R^3$, and $R^4$ are the same or different and are selected from the group consisting of hydrogen and $C_1$–$C_{20}$ alkyl.

The oxidizing agent employed in the process of this invention is a hydrogen peroxide source such as hydrogen peroxide ($H_2O_2$) or a hydrogen peroxide precursor (i.e., a compound which under the epoxidation reaction conditions is capable of generating or liberating hydrogen peroxide).

The amount of hydrogen peroxide relative to the amount of olefin is not critical, but most suitably the molar ratio of hydrogen peroxide:olefin is from 100:1 to 1:100 when the olefin contains one ethylenically unsaturated group. The molar ratio of ethylenically unsaturated groups in the olefin substrate to hydrogen peroxide is more preferably in the range of from 1:10 to 10:1. One equivalent of hydrogen peroxide is theoretically required to oxidize one equivalent of a monounsaturated olefin substrate, but it may be desirable to employ an excess of one reactant to optimize selectivity to the epoxide. In particular, the use of a slight to moderate excess (e.g., 5 to 50%) of olefin relative to hydrogen peroxide may be advantageous for certain substrates.

Although the hydrogen peroxide to be utilized as the oxidizing agent may be derived from any suitable source, a distinct practical advantage of the process of this invention is that the hydrogen peroxide may be obtained by contacting a secondary alcohol such as alpha-methyl benzyl alcohol, isopropyl alcohol, 2-butanol or cyclohexanol with molecular oxygen under conditions effective to form an oxidant mixture comprised of secondary alcohol and hydrogen peroxide (and/or hydrogen peroxide precursors). Typically, such an oxidant mixture will also contain a ketone such as acetophenone, acetone, or cyclohexanone corresponding to the secondary alcohol (i.e., having the same carbon skeleton), minor amounts of water, and varying amounts of other active oxygen species such as organic hydroperoxides. Molecular oxygen oxidation of anthrahydroquinone, alkyl-substituted anthrahydroquinones, or water-soluble anthrahydroquinone species may also be employed to generate the hydrogen peroxide oxidant. The hydrogen peroxide may be generated in situ immediately prior to or simultaneous with epoxidation, as described, for example, in European Pat. Publication No. 526,945, Japanese Kokai No. 4-352771, and Termini et al., "Catalytic Oxidation of Alkanes Using Titanium Silicate in the Presence of In-Situ Generated Hydrogen Peroxide," DGMK Conference on Selective Oxidations in Petrochemistry, Sep. 16–18, 1992, pp. 205–213, and European Pat. Publication No. 469,662.

If desired, a solvent may additionally be present during the epoxidation process of this invention in order to dissolve the reactants other than the modified titanium-containing catalyst, to provide better temperature control, or to favorably influence the epoxidation rates and selectivities. The solvent, if present, may comprise from 1 to 99 weight percent of the total epoxidation reaction mixture and is preferably selected such that it is a liquid at the epoxidation reaction temperature. Organic compounds having boiling points at atmospheric pressure of from about 25° C. to 300° C. are generally preferred for use. Excess olefin may serve as a solvent or diluent. Illustrative examples of other suitable solvents include, but are not limited to, ketones (e.g., acetone, methyl ethyl ketone, acetophenone), ethers (e.g., tetrahydrofuran, butyl ether), nitriles (e.g., acetonitrile), aliphatic and aromatic hydrocarbons, halogenated hydrocarbons, and alcohols (e.g., methanol, ethanol, isopropyl alcohol, t-butyl alcohol, alpha-methyl benzyl alcohol, cyclohexanol). An important practical advantage of the present invention is that it may readily be practiced using bulkier alcohol solvents such as alpha-methyl benzyl alcohol, whereas poor results are obtained with such solvents when other titanium-containing molecular sieves such as TS-1 are utilized as catalyst. This flexibility minimizes the problems which might otherwise be encountered when trying to separate the epoxide product from the epoxidation reaction mixture. Quantitative removal of methanol, for example, from a relatively light epoxide such as propylene oxide is difficult due to the similarity in their boiling points. More than one type of solvent may be utilized. Water may also be employed as a solvent or diluent; surprisingly, the process of the invention proceeds with minimal hydrolysis even when a significant quantity of water is present in the epoxidation reaction mixture. Biphasic as well as monophasic reaction systems thus are possible using the present invention.

In one embodiment of the invention, the ammonium, alkali metal or alkaline earth-modified titanium-containing molecular sieve is generated in-situ during epoxidation through the use of an unmodified (e.g., highly protonated) titanium-containing molecular sieve in combination with either an ammonium, alkali metal or alkaline earth compound of the type described previously or a buffer comprised of an alkali metal or alkaline earth salt of a carboxylic acid or the like. For example, the reaction medium wherein the olefin is contacted with hydrogen peroxide may contain a NaOAc/HOAc buffer system (preferably, 0.1 to 5M) in a suitable solvent such as an alcohol (e.g., methanol). Alternatively, an alkali metal compound alone such as sodium acetate could be utilized. In a batch process, the ammonium, alkali metal or alkaline earth compound could, for example, be added by itself prior to initiation of epoxidation while in a continuous process (as when a CSTR reactor is employed) such compound could be combined with one of the feed streams containing one of the other reaction components such as the hydrogen peroxide.

The reaction temperature is not critical, but should be sufficient to accomplish substantial conversion of the olefin to epoxide within a reasonably short period of time. It is generally advantageous to carry out the reaction to achieve as high a hydrogen peroxide conversion as possible, preferably at least 50%, more preferably at least 90%, most preferably at least 95%, consistent with reasonable selectivities. The optimum reaction temperature will be influenced by catalyst activity, olefin reactivity, reactant concentrations, and type of solvent employed, among other factors, but typically will be in a range of from about 0° C. to 150° C. (more preferably, from about 25° C. to 120° C.). Reaction or residence times of from about 1 minute to 48 hours (more desirably, from about 10 minutes to 8 hours) will typically be appropriate, depending upon the above-identified variables. Although sub-atmospheric pressures can be employed, the reaction is preferably (especially when the boiling point of the olefin is below the epoxidation reaction temperature) performed at atmospheric pressure or at elevated pressure (typically, between 1 and 100 atmospheres). Generally, it will be desirable to pressurize the epoxidation vessel sufficiently to maintain the reaction components as a liquid phase mixture. Most (i.e., over 50%) of the olefin should preferably be present in the liquid phase.

The process of this invention may be carried out in a batch, continuous, or semi-continuous manner using any appropriate type of reaction vessel or apparatus such as a fixed bed, transport bed, fluidized bed, stirred slurry, or CSTR reactor in a monophase or biphase system. Known methods for conducting metal-catalyzed epoxidations of olefins using hydrogen peroxide will generally also be suitable for use in this process. Thus, the reactants may be combined all at once or sequentially. For example, the hydrogen peroxide or hydrogen peroxide precursor may be added incrementally to the reaction zone. The hydrogen peroxide could also be generated in situ within the same reactor zone where epoxidation is taking place. Once the epoxidation has been carried out to the desired degree of conversion, the epoxide product may be separated and recovered from the reaction mixture using any appropriate technique such as fractional distillation, extractive distillation, liquid-liquid extraction, crystallization, or the like. After separating from the epoxidation reaction mixture by any suitable method such as filtration, the recovered catalyst may be economically re-used in subsequent epoxidations. Where the catalyst is deployed in the form of a fixed bed, the epoxidation product withdrawn as a stream from the epoxidation zone will be essentially catalyst-free with the catalyst being retained within the epoxidation zone. In certain embodiments of the instant process where the epoxide is being produced on a continuous basis, it may be desirable to periodically or constantly regenerate all or a portion of the used titanium-containing molecular sieve catalyst in order to maintain optimum activity and selectivity. Suitable regeneration techniques include, for example, treating the catalyst with solvent, calcining the catalyst, and/or contacting the catalyst with an ammonium, alkali metal or alkaline earth compound to replace any ammonium or Group IA or IIA cations which may gradually be lost during epoxidation. Any unreacted olefin or hydrogen peroxide may be similarly separated and recycled. Alternatively, the unreacted hydrogen peroxide (especially if present at concentrations too low to permit economic recovery) could be thermally or chemically decomposed into non-peroxy species such as water and oxygen, for example. In certain embodiments of the process where the hydrogen peroxide is generated by molecular oxygen oxidation of a secondary alcohol, the crude epoxidation reaction mixture will also contain a secondary alcohol and a ketone corresponding to the secondary alcohol. After separation of the epoxide from the secondary alcohol and the corresponding ketone, the ketone may be converted back to secondary alcohol by hydrogenation. For example, the ketone may be reacted with hydrogen in the presence of a transition metal hydrogenation catalyst such as a Raney nickel, copper chromite, ruthenium, platinum or palladium catalyst. Hydrogenation reactions of this type are well known to those skilled in the art. The secondary alcohol may also be dehydrated using known methods to yield valuable alkenyl products such as styrene.

From the foregoing description, one skilled in the art can readily ascertain the essential characteristics of this invention, and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

A sodium-modified titanium-containing molecular sieve catalyst was prepared by first synthesizing protonated titanium silicoaluminate following the procedures described in Camblor et al., Zeolites 13, pp. 82–87 (1993) and then exchanging the proton countercations by stirring the calcined titanium-substituted zeolite beta with 1M aqueous sodium acetate at 80° C. for four hours. After washing thoroughly with water, the titanium-containing molecular sieve was dried at 120° C. and then calcined at 550° C. for 5 hours.

To demonstrate the effectiveness of the modified titanium-containing molecular sieve as an epoxidation catalyst, 1-hexene (16.5 m mole) was combined with methanol solvent (12.2 g), hydrogen peroxide (4.5 m mole), and catalyst (0.10 g) and heated at 60° C. for the time specified in Table 1.

TABLE 1

| Time, hr. | % $H_2O_2$ Selectivity[a] | % Olefin Conversion | % Epoxide Selectivity[b] | % Glycol Ethers Selectivity[b] |
|---|---|---|---|---|
| 1 | 11 | 0.5 | 95 | 5 |
| 3 | 14 | 2 | 93 | 7 |
| 6 | 10 | 3 | 93 | 7 |

[a]based on the total equivalents of both epoxide and glycol ethers formed
[b]based on olefin converted A more active, but less selective, catalyst is obtained if the protonated titanium silicoaluminate is exposed to 0.5% aqueous sodium acetate for 12 hours.

For comparative purposes, epoxidation of 1-hexene was attempted under the same conditions but using unmodified (protonated) titanium-silicoaluminate (i.e., not treated with an ammonium, alkali metal or alkaline earth metal compound to exchange hydrogen cation). As indicated in Table II, the unmodified titanium-silicoaluminate (containing relatively high levels of aluminum) was found to provide unacceptably low selectivity to epoxide, although a higher rate of olefin conversion was observed. Most of the olefin was converted to glycol ether, indicating that the titanium silicoaluminate was catalyzing the ring-opening of epoxide with the methanol solvent.

TABLE II

| Time, hr. | % Olefin Conversion | % Epoxide Selectivity[b] | % Glycol Ethers Selectivity[b] |
|---|---|---|---|
| 1 | 7 | 19 | 81 |
| 3 | 15 | 4 | 96 |
| 6 | 14 | 1 | 99 |

[b]based on olefin converted

EXAMPLE 2

This example demonstrates the preparation of a titanium-containing molecular sieve from zeolite beta by a dealumination technique and its utility as an olefin epoxidation catalyst.

Calcined zeolite beta (5 g; Conteka 41-89-001) having a $SiO_2:Al_2O_3$ ratio of 24 was added to 500 mL of a 13N nitric acid solution. The resultant suspension was heated at 80° C. for four hours with stirring. The suspended solids were recovered by filtration, washed well with deionized water, and dried at 95° C. overnight to provide partially dealuminated zeolite beta (elemental analysis: Si/Al=725). The partially dealuminated zeolite beta (3 g) was added to a fitted quartz tube. The tube was loaded vertically in a furnace and a slow (100 cc/min) nitrogen flow initiated. The sample was heated at 400° C., then heated to 580° C. and the nitrogen flow increased to 300 cc/min. Once the temperature had stabilized at 580° C., the sample was treated with titanium tetrachloride for six hours by sparging the nitrogen feed through a warmed (40° C.) $TiCl_4$ solution. After this time $TiCl_4$ treatment was discontinued and nitrogen flow through the sample continued at 580° C. for an additional hour. The sample was then cooled to room temperature overnight with continuous nitrogen flow. The cooled sample was treated with a 1M solution of ammonium nitrate at 80° C. for four hours. The sample was recovered by filtration, washed well with water, dried at 95° C. and then calcined at 550° C. for six hours to yield a titanium-containing molecular sieve product having the following chemical composition: 39% Si, 0.05% Al, 3.4% Ti; Si/Al=780; Si/Ti=20. The powder x-ray diffraction pattern was consistent with a crystalline beta structure (no structural degradation was apparent).

A series of 1-hexene epoxidations using the titanium-containing molecular sieve thus obtained or an alkali metal modified version thereof was performed using the following reaction conditions: 60° C., 12.2 g methanol (solvent), 16.5 m mol 1-hexene, 4.5 m mol hydrogen peroxide, 0.10 g catalyst. The results obtained are shown in Table III.

Example 2-A demonstrates that while the unmodified titanium-containing molecular sieve is fairly active (i.e., the rate of hydrogen peroxide reaction is rapid), it provides poor selectivity to the desired 1-hexene oxide with the major products formed being glycol ethers. The beneficial effect of having an alkali metal-containing buffer present during epoxidation is shown in Example 2-B wherein much higher epoxide selectivity was observed while maintaining good catalyst activity (as reflected in the 1-hexene and hydrogen peroxide conversions achieved after 6 hours). The results observed in Example 2-D indicate that comparable improvements may also be realized by pre-treating the titanium-containing molecular sieve with dilute aqueous sodium acetate prior to use in the process of the invention, although Example 2-C suggests that the catalyst activity may be adversely affected when a higher concentration of sodium acetate is employed.

TABLE III

| Example | Catalyst Treatment | Buffer Present | Time, hr | $H_2O_2$ Conversion % | Epoxide Selectivity, %[d] | Glycol Ether Selectivity, %[d] | Hexene Conversion, % | Epoxide/Glycol Ether Ratio |
|---|---|---|---|---|---|---|---|---|
| 2-A | None | No | 1 | 31 | 35 | 37 | 6 | 0.9 |
|  |  |  | 6 | 91 | 7 | 82 | 16 | 0.1 |
| 2-B | None | Yes[c] | 1 | 74 | 81 | 2 | 16 | 25 |
|  |  |  | 6 | 99 | 64 | 14 | 21 | 4 |
| 2-C | a | No | 1 | Trace | — | — | — | — |
|  |  |  | 6 | 30 | 32 | Trace | 3 | 100 |
| 2-D | b | No | 1 | 55 | 80 | 2 | 13 | 40 |
|  |  |  | 6 | 96 | 88 | 6 | 27 | 14 | a. washed 12 hours at 80° C. with 1M aq. sodium acetate
b. washed 12 hours at 80° C. with 0.5% aq. sodium acetate
[c] 0.5% acetic acid/sodium acetate buffer in methanol
[d] based on hydrogen peroxide

We claim:

1. A process for epoxidation of an olefin comprising contacting said olefin with hydrogen peroxide in the presence of a catalytically effective amount of a crystalline titanium-containing molecular sieve characterized by a framework structure isomorphous to zeolite beta comprised of Si, Ti and Al atoms and containing a plurality of aluminum-associated cationic sites, wherein 25 to 100% of the cations present at such cationic sites are ammonium cations, alkali metal cations, or alkaline earth metal cations and 0 to 75% of the cations are hydrogen cations, for a time and at a temperature effective to selectively form an epoxide of the olefin.

2. The process of claim 1 wherein the titanium-containing molecular sieve has a Si:Al molar ratio of greater than 25 but less than 1000.

3. The process of claim 1 wherein the olefin is a $C_2$–$C_{10}$ aliphatic mono-olefin.

4. The process of claim 1 wherein the temperature is from 25° C. to 150° C.

5. The process of claim 1 wherein the hydrogen peroxide is obtained by molecular oxygen oxidation of a secondary alcohol.

6. The process of claim 1 wherein said contacting is carried out in a liquid phase.

7. The process of claim 1 wherein from 0.001 to 10 grams of the crystalline titanium-containing molecular sieve per mole of olefin is utilized.

8. The process of claim 1 wherein at least 75% of said cations are alkali metal cations, said alkali metal cations being selected from sodium cations, potassium cations, and combinations thereof.

9. The process of claim 1 wherein the titanium-containing molecular sieve has the general formula $SiO_2$:$xAl_2O_3$:$yTiO_2$ wherein x is from 0.005 to 0.2 and y is from 0.01 to 0.2.

10. A process for epoxidation of a $C_2$–$C_{10}$ aliphatic mono-olefin comprising contacting said mono-olefin with hydrogen peroxide in a liquid phase in the presence of from 0.001 to 10 grams per mole of olefin of a crystalline titanium-substituted zeolite beta characterized by a framework structure isomorphous to zeolite beta and comprised of Si, Ti and Al atoms, wherein the Si:Al molar ratio is greater than 25 but less than 1000, and containing a plurality of aluminum-associated cationic sites, wherein 75 to 100% of the cations present at such cationic sites are sodium cations or potassium cations and 0 to 25% of the cations are hydrogen cations, at a temperature of from 25° C. to 120° C. for a time effective to selectively form an epoxide of the mono-olefin.

11. The process of claim 10 wherein the $C_2$–$C_{10}$ aliphatic mono-olefin is propylene.

12. The process of claim 10 wherein the hydrogen peroxide is obtained by molecular oxygen oxidation of an alcohol selected from alpha-methyl benzyl alcohol, anthrahydroquinone, alkyl-substituted anthrahydroquinones, water-soluble anthrahydroquinone species, sec-butyl alcohol, cyclohexanol, and isopropanol.

13. The process of claim 10 wherein the crystalline titanium-containing molecular sieve is generated in-situ using an alkali metal-containing buffer in combination with a protonated titanium-containing molecular sieve characterized by a framework structure isomorphous to zeolite beta and comprised of Si, Ti and Al atoms wherein the Si/Al molar ratio is greater than 25 but less than 1000 and a plurality of aluminum-associated cationic sites are present, with greater than 25% of the cations present at such cationic sites being hydrogen cations.

14. The process of claim 10 wherein the titanium-containing molecular sieve is obtained by
(a) subjecting a mixture comprised of water, a titanium source selected from titanium halides and titanium tetraalkoxides, a quaternary ammonium or phosphonium salt template, an aluminum salt, and a silica source selected from tetraalkyl orthosilicates, silicates, and silica gel to hydrothermal treatment at a temperature in the range of 75° C. to 200° C. for a time effective to obtain precipitated crystals and a mother liquor;
(b) separating said crystals from the mother liquor;
(c) heating said crystals at a temperature at a temperature of 350° C. to 800° C. effective to obtain calcined crystals essentially free of quaternary ammonium or phosphonium salt template and having aluminum-associated cationic sites wherein the cations present at said cationic sites are hydrogen cations; and
(d) contacting said calcined crystals with an alkali metal compound under conditions effective to replace at least 75% of the hydrogen cations with alkali metal cations.

15. The process of claim 10 wherein the titanium-substituted zeolite beta is obtained by
(a) contacting a zeolite beta with a mineral acid to form a partially dealuminated zeolite beta having a Si/Al molar ratio of greater than 25 but less than 1000;
(b) contacting the partially dealuminated zeolite beta with a titanium source to form a protonated titanium-substituted zeolite beta and
(c) contacting the protonated titanium silicoaluminate with an alkali metal compound under conditions effective to replace at least 75% of the hydrogen cations in said protonated titanium-substituted zeolite beta with alkali metal cations.

* * * * *